US012714770B2

(12) United States Patent
Müller et al.

(10) Patent No.: US 12,714,770 B2
(45) Date of Patent: Aug. 25, 2026

(54) METHOD AND DEVICE FOR DISCONNECTION

(71) Applicant: FRESENIUS MEDICAL CARE DEUTSCHLAND GMBH, Bad Homburg (DE)

(72) Inventors: Stefan Müller, Dingolshausen (DE); Martin Thys, Grettstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 462 days.

(21) Appl. No.: 18/546,790

(22) PCT Filed: Feb. 16, 2022

(86) PCT No.: PCT/EP2022/053718

§ 371 (c)(1),
(2) Date: Aug. 17, 2023

(87) PCT Pub. No.: WO2022/175289

PCT Pub. Date: Aug. 25, 2022

(65) Prior Publication Data

US 2024/0131240 A1 Apr. 25, 2024
US 2024/0226400 A9 Jul. 11, 2024

(30) Foreign Application Priority Data

Feb. 18, 2021 (DE) .................... 10 2021 103 885.5

(51) Int. Cl.
*A61M 1/16* (2006.01)

(52) U.S. Cl.
CPC ..... *A61M 1/1621* (2014.02); *A61M 2205/502* (2013.01)

(58) Field of Classification Search
CPC .............. A61M 1/1621; A61M 1/1623; A61M 1/1635; A61M 1/1637; A61M 1/1641; A61M 1/301; A61M 2205/502
See application file for complete search history.

(56) References Cited

U.S. PATENT DOCUMENTS 4,331,540 A 5/1982 Witsoe
2015/0129498 A1* 5/2015 Mishima ............ A61M 1/3644 210/646

FOREIGN PATENT DOCUMENTS

DE 10 2007 024 463 11/2008
DE 10 2009 024 575 12/2010
(Continued)

OTHER PUBLICATIONS

Office Action issued in corresponding Japanese Patent Application 2023-550033 issued Dec. 22, 2025 (4 pages).

*Primary Examiner* — Philip R Wiest
(74) *Attorney, Agent, or Firm* — Kilyk & Bowersox, P.L.L.C.

(57) ABSTRACT

The invention relates to a medical apparatus designed to receive a detachable fluid-conducting first line portion (3). The medical apparatus comprises a second line portion (2) designed to be connected to the first line portion (3), wherein a movable element (38) is situated in the second line portion (2), by means of which movable element the second line portion (2) is separated into a first sub-portion (2*a*) and a second sub-portion (2*b*). In addition, the medical device comprises: at least a first and a second blocking element (7, 8) for enclosing a fluid volume in the first line portion (3) and the second line portion (2); and a pump (6) for generating a vacuum in a first of the two sub-portions (2*a*, 2*b*) of the second line portion (2), as a result of which elastic deformation takes place in and/or on the second of the two sub-portions (2*a*, 2*b*) and the movable element (38) is
(Continued)

Figure 1:
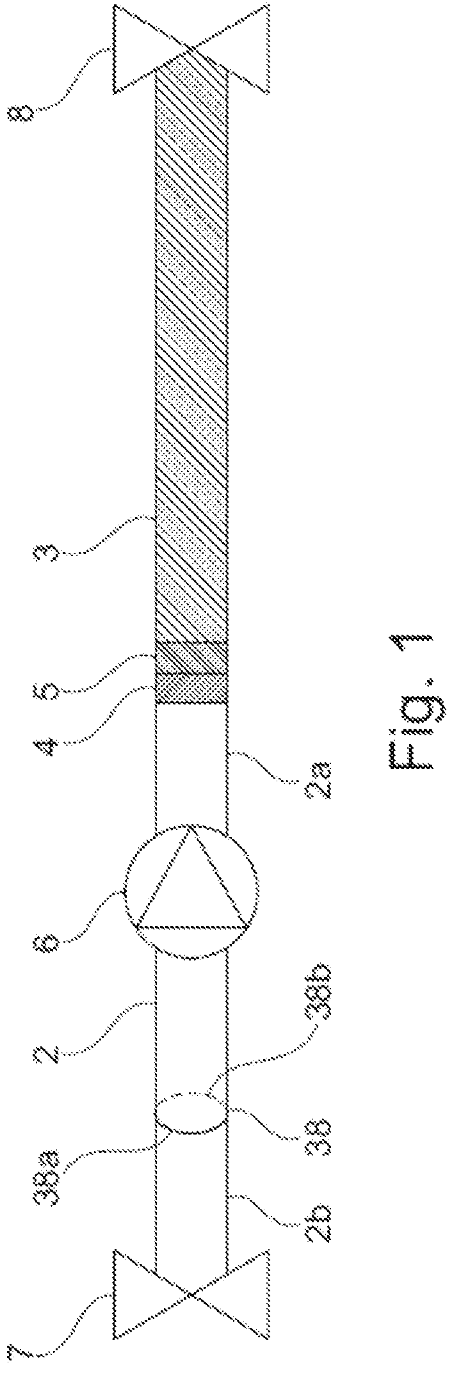

moved; and a controller for controlling the pump (6), wherein the controller is programmed, in a disconnection mode, to operate the pump (6) to generate the vacuum.

20 Claims, 9 Drawing Sheets

(56) References Cited

FOREIGN PATENT DOCUMENTS

| | | | | |
|---|---|---|---|---|
| DE | 10 2013 106 830 | | | 1/2015 |
| JP | 2010184029 | A | | 8/2010 |
| JP | 5356853 | | | 12/2013 |
| JP | 5356853 | B2 | * | 12/2013 |
| WO | 2021/245110 | | | 12/2021 |

* cited by examiner

METHOD AND DEVICE FOR DISCONNECTION

The present invention relates to a method for detaching (disconnecting) two fluid-carrying line sections of a medical device, and to a medical device adapted to perform a method according to the invention.

When disconnecting fluid-carrying line sections of medical devices from each other, such as a machine-side fluidic system from a fluidic system intended for single-use (disposable) of extracorporeal blood treatment machines or dialysis machines, high hygiene standards must be maintained to ensure patient safety.

In practice, for example, after extracorporeal blood treatment, when a tube set is decoupled from a blood treatment machine, liquid contained in the tube set can enter the device-side fluid circuit or hydraulics of the device and contaminate them, necessitating elaborate disinfection procedures for the blood treatment machine.

Before the start of a treatment, after completion of a priming process (filling and flushing process of a fluid line system with physiological liquid), air, for example in the form of air bubbles, may be present in the liquid in the fluidic system of a medical device or contamination may be present. If the fluidic system is separated to connect a portion of the fluidic system to a patient, as little air as possible should remain in the portion of the fluidic system to be connected to the patient. If air or contaminants remain in the part of the fluidic system to be connected to the patient, they can enter the patient's bloodstream.

Furthermore, it is desirable, in particular in the medical field, that leaks are avoided for hygienic reasons during any disconnection of fluid-carrying lines.

Thus, the object underlying the present invention is to mitigate or even completely eliminate the problems of the prior art. In particular, the object underlying the present invention is to provide a method for more hygienic disconnection of fluid connections and a corresponding medical device. A further object of the present invention is to reduce the entry of air into at least one line section during disconnection.

This object is achieved by the subject matters of the independent claims. Advantageous further developments of the invention are the subject matter of the sub-claims.

A first aspect of the invention relates to a medical device configured to receive a detachable fluid-carrying first line section, comprising a second line section configured for connecting to the first line section, wherein a displaceable member is arranged in the second line section, by means of which the second line section is sub-divided into a first sub-section and a second sub-section, at least a first and a second shut-off element for enclosing a fluid volume in said first line section and in the second line section, a pump for generating a negative pressure in a first of the two sub-sections of the second line section, thereby effecting an elastic deformation in and/or at the second of the two sub-sections while moving the displaceable member, and a controller for actuating the pump, wherein the controller is programmed to operate the pump in a disconnection mode to generate the negative pressure.

For example, the displaceable member is displaced toward a connection point of the first and second line sections when a negative pressure is generated between the connection point and the displaceable member in the second line section.

The displaceable member sub-divides the line section, for example the second line section, into two sub-sections. The reversible movement of the displaceable member reduces the volume of the first sub-section between the displaceable member and the connection point of the first and second line sections.

Upon disconnection of the first and second line sections, pressure equalization occurs and the displaceable member moves back towards its initial position or to its initial position, which is why the volume of the first sub-section between the displaceable member and the connection point of the first and second line sections increases again, so that fluid is drawn away from the connection point into the first sub-section.

In this case, the displaceable member is preferably hydraulically permeable and fluidically non-permeable and preferably transfers the negative pressure generated by means of the pump from one of the two sub-sections to the other one of the two sub-sections. However, the two sub-sections are here preferably always fluidically separated from each other by the displaceable member. The fluidic separation by the displaceable member makes it possible that, by means of the displaceable member, a circuit of the medical device with fresh uncontaminated liquid, for example freshwater or fresh dialysis solution, is always separated from a circuit of the medical device with used, potentially contaminated liquid, for example used water or used dialysis solution. In other words, the first sub-section may comprise an area of the circuit that is subject to lower sanitary requirements than the second sub-section.

It has proven advantageous in practice if the displaceable member is at least partially formed by a balancing system of the medical device and/or preferably comprises or consists of a membrane, in particular a fluidically impermeable, elastically deformable membrane, for example of the balancing system or a separately provided membrane separating the second line section.

Alternatively or in addition, the displaceable member may comprise or consist of a movable ball and/or piston.

In some balancing systems, pistons are used in combination with flow sensors. However, the use of pistons has the disadvantage that the inner wall of a hollow cylinder in which the piston moves is exposed alternately to the service water side and the freshwater side of a medical device, for example, as the piston moves. This poses a higher risk of contamination in contrast to the use of a membrane, which always completely fluidically separates the service water side and the freshwater side from each other. In other words, with a membrane, the edge of the membrane is always connected to the same area of the wall of the sub-section.

Furthermore, in a medical device according to the invention, the controller can be programmed to close at least one of the shut-off elements for closing off the fluid volume on one side before the negative pressure is generated and/or to close one of the shut-off elements for enclosing the fluid volume after the negative pressure is generated. Alternatively or additionally, at least one of the shut-off elements can also be closed manually.

According to one embodiment, the second line section is part of a fixedly-installed device-side fluidic system of the medical device.

The first and/or the second line section may also have one or more branches. In order to generate the negative pressure or to maintain it, each branch of these branched line sections can be shut off by shut-off elements provided on the line sections.

In a medical device according to the invention, the controller may be programmed to close all necessary shut-off elements required to achieve a negative pressure in a line system comprising at least the first and second line sections, or in other words, to prevent pressure equalization between the negative pressure region and another region of the circuit. It is known to a person skilled in the art to close-off sections of a line system to maintain a negative pressure there.

The medical device according to the invention may further comprise a fluid source, in particular a fluid source for a physiological liquid, fluidically connected to the second sub-section, optionally a sterile filter fluidically disposed between and connected to the fluid source and the second sub-section, and a medical device-side connector at an end of the second sub-section for connecting to an end of the first line section.

Furthermore, a medical device according to the invention may preferably further comprise a discharge line, wherein the first sub-section is fluidically connected to or is a part of the discharge line.

Furthermore, a medical device according to the invention may be provided with at least one direct connecting line between the first sub-section and the second sub-section and a valve for opening and closing the connecting line, and the controller may be programmed to shut off the at least one connecting line in the disconnection mode.

In other words, a medical device according to the invention may comprise one or more connecting lines or short-circuit lines between a circuit of the medical device with fresh uncontaminated liquid, for example freshwater or fresh dialysis solution, and a circuit of the medical device with used potentially contaminated liquid, for example used water or used dialysis solution. To avoid potential contamination of the medical device circuit with fresh uncontaminated liquid by liquid from the medical device circuit with used potentially contaminated liquid during the disconnection process of the first and second line sections, the controller may be programmed to shut off any interconnecting lines or short-circuit lines present during the disconnection process of the first and second line sections.

According to one embodiment of the invention, the pump to be used in the context of the invention is a peristaltic pump and at least one actuator of the peristaltic pump is a part of the first or second shut-off element or is the first or second shut-off element.

According to one embodiment of the invention, the pump to be used in the context of the invention is a diaphragm pump which is optionally arranged on the first sub-section, in particular on a branch line. In other words, the first sub-section may have a branch and the diaphragm pump may be arranged at a line section connected to a branch of the sub-section other than the branch in which the displaceable member is arranged.

According to one embodiment of the invention, the pump is an ultrafiltration pump or a flow pump, blood pump or substituate pump or balance chamber pump of an extracorporeal blood treatment device, in particular a dialysis device.

The ultrafiltration pump can be the diaphragm pump and the displaceable member can be a membrane of a balance chamber.

Further, a medical device according to the invention may comprise a user interface for inputting an instruction by a user, wherein the controller is programmed to activate the disconnection mode or to start the pump in response to an input of the instruction at the user interface.

When activating the disconnection mode, a special mode can be activated in the program code of the controller. When the disconnection mode is activated, a special sequence of a program code can run, with which the medical device performs the disconnection procedure. The disconnection mode may also be integrated into another mode. For example, a priming mode may be stored in the program code and the disconnection mode may represent a step, such as the final step, of the priming mode.

In the disconnection mode, the controller can actuate the pump to create the negative pressure and/or actuate the shut-off element(s) to shut off the corresponding line.

The user interface may include a display, a screen, a touch screen, a keyboard, a control button, a microphone for recording a voice signal, a camera for detecting a gesture of the user.

The controller may be programmed to activate a plurality of modes and automatically perform a switchover from one of the modes to the disconnection mode.

For example, in a so-called reinfusion mode, the controller can be connected to a sensor of the medical device, for example an optical sensor, which detects that there is no more blood in the set of tubes. The controller can process this signal in its program code in such a way that a further mode can be started. This mode may be the disconnection mode. Alternatively or additionally, an additional mode can be provided in the program code of the controller, which involves emptying the tube set and/or a dialyzer and/or a machine-side fluid system after completion of the reinfusion mode, and the controller can be programmed to switch to the disconnection mode after a predetermined time interval or after a predetermined fluid volume has been transported or after air or an interface between blood and a reinfusion liquid with optical properties other than blood has been detected in the area to be emptied by means of a sensor or after a predetermined pressure is detected.

Alternatively or additionally, a mode ("priming mode") may be provided in the program code of the controller which—before the start of the treatment—fills the tube set or cassette with priming liquid and/or flushes the tube set or cassette with liquid, and the controller may be programmed to switch to the disconnection mode after completion of the priming mode. The controller may be programmed to operate a pump during the priming mode, thereby displacing liquid from a liquid source toward the tube set or cassette. The controller may be programmed to detect an end of priming, for example, when a predetermined time has elapsed, a predetermined liquid volume has been displaced into the tube set or cassette, an air detector or liquid sensor indicates that no more air or predominantly only liquid is present.

The controller can also be programmed in such a way that it first automatically switches to disconnection mode, but the pump is only started after a corresponding input via the user interface.

The controller may further be programmed to allow input via the user interface to start the pump, in particular only when the disconnection mode is activated. In other words, the program code of the controller may provide that there are modes or phases, other than the disconnection mode, in which starting of the pump does not occur despite corresponding input via the user interface.

With such a limitation on allowing the disconnection procedure to be started, it may be possible to prevent such a disconnection procedure from being started during a treatment, for example.

A medical device according to the invention may further comprise an output unit that indicates to a user, for example, whether disconnection of the first and second line sections can or should occur. For example, a user may be prompted to disconnect the first and second line sections when a sufficient negative pressure has been generated in the sub-section or the displaceable member is in the displaced position. Alternatively or additionally, a user may be advised not to disconnect the first and second line sections if sufficient negative pressure has not been generated in the sub-section or the displaceable member is not in the displaced position. The indication may be provided, for example, by a message on a screen.

For example, the controller may comprise a computer system and may be implemented in the form of digital circuitry, computer hardware, firmware, software, or any combination thereof. The invention may further be implemented in the form of a computer program product, such as a computer program on a physical information carrier (e.g., machine-readable storage medium). The controller may include a general-purpose processor, a digital signal processor (DSP) for continuously processing digital signals, a microprocessor, an application-specific integrated circuit (ASIC), a field programmable gate array (FPGA) consisting of logic elements, or other integrated circuits (IC) or hardware components to perform the individual process steps. A data processing program (software) may run on the hardware components to perform the process steps. It is also possible to have a plurality or combination of the various components to control their operation.

The controller may further comprise a memory in which the program code is stored, for example a read-only memory (ROM) or random access memory (RAM) or both, magnetic, magneto-optical, optical or solid state (SSD) storage media, non-volatile storage elements such as semiconductor storage elements (e.g. EPROM, EEPROM), flash memory devices, magnetic or magneto-optical storage media, CD-ROM, DVD-ROM or Blue-Ray disks. Storage can also be provided on demand or accessible via the Internet (e.g., cloud computing). Suitable storage media for storing program instructions and data include all types of non-volatile memory elements such as semiconductor memory elements (e.g., EPROM, EEPROM), flash memory devices, magnetic or magneto-optical storage media, CD-ROM, DVD-ROM, or Blu-Ray discs. The processor and memory elements can be supplemented by special logic modules or form part thereof.

Preferably, in a medical device according to the invention, one line section of the two line sections is part of a disposable, in particular a tube set or cassette system used in the context of blood treatment, or optionally both line sections are part of one or more disposables, in particular a tube set or cassette system used in the context of blood treatment. Optionally, only the first line section is part of or itself a disposable.

Another aspect of the invention relates to a disposable, in particular a tube or a tube set, which can be used in the context of a medical device according to the invention.

This disposable may be provided in combination with the features of the medical device set forth above, or as a stand-alone unit. The disposable may be provided in combination with the medical device having the displaceable member that is displaced upon disconnection, and with a medical device without a displaceable member that is displaced upon disconnection. Further, the disposable is described with reference to the medical device of the invention having the displaceable member that is displaced upon disconnection, but the description is equally applicable to the medical device without a displaceable member that is displaced upon disconnection.

The disposable, which can be used in the medical device, for example, can have a tube or consist of a tube or be a sub-section of a tube. The disposable may have a volume change of from 1 to 5000 cubic millimeters, in particular from 1 to 1000 cubic millimeters, in particular from 1 to 500 cubic millimeters, in particular from 200 to 500 cubic millimeters, in particular from 350 to 475 cubic millimeters, when negative pressure less than −200 mbar is applied. The volume change may occur in a section of the tube to which the negative pressure is applied. The values may refer to that portion of the disposable which, when the disposable is used as intended, is disposed between a connection point to the medical device and a tubing clamp terminating the tube. This disposable may form the first line section, or the first line section may be a part of this disposable, or the disposable may be a part of this first line section. In particular, the volume change may occur over a length of the tube as described below.

The tube may be a conduit that, when used during extracorporeal treatment, has one end connected to a dialyzer and a second end connected to a patient's vascular system. The tube may include or be in fluidic communication with a venous drip chamber.

The negative pressure at which this volume change occurs may be a predetermined negative pressure stored in the program code of the medical device controller, and the controller may be programmed to generate this predetermined negative pressure in the first line section.

The negative pressure may be a value of or less than −500 mbar, −200 mbar, −175 mbar, or −120 mbar. Negative pressure can refer to a pressure compared to atmospheric pressure. When the sign "−" is used in connection with pressure specifications, it means "minus".

In a medical device according to the present invention, an adapter may be arranged between the first line section and the second line section, and the controller may be programmed to generate a predetermined negative pressure in the first line section in a disconnection mode, wherein the volume change of the first line section upon application of the negative pressure is less than an internal volume of the adapter, preferably wherein the internal volume of the adapter is constant. In other words, while the volume of the first line section may change upon application of negative pressure, the internal volume of the adapter may remain substantially constant. When an "internal volume" or "volume" of the adapter is referred to in the remainder of the description, it preferably refers to the volume that is in fluidic communication with the line sections connected or to be connected to the adapter.

The disposable, in particular the tube, can be connected to the medical device by means of an adapter and be designed in such a way that a volume change of the part of the tube belonging to the first line section to which negative pressure has been applied is smaller than a volume of the adapter when the tube is disconnected from another line section, wherein the volume of the adapter is preferably constant or changes only very slightly during the disconnection. The adapter may be made of a material that has a lower compliance than the tube. The adapter may have a compliance per unit length that is lower than the compliance of the tube by at least a factor of 10, in particular at least a factor of 20.

The adapter can be made of a rigid material, for example hard plastic, so that the volume of the adapter does not change or does not change noticeably due to the negative pressure. The adapter may be straight or angled between two openings, preferably rectangular, i.e. two openings of the adapter may be oriented at right angles to each other. The adapter may have an internal volume between the two openings of from 10 ml to 10000 ml, in particular from 200 ml to 1000 ml, in particular from 300 to 600 cubic millimeters, in particular from 400 to 600 cubic millimeters, in particular from 450 to 600 cubic millimeters. The dimension of the adapter between the two openings can be between 4 cm and 8 cm, preferably between 5 and 7 cm. The ratio of the length of the internal volume of the adapter to the inner diameter of the internal volume of the adapter can be between 3 to 500, in particular between 5 to 30. In this context, the internal volume may be straight or have a bend, in particular a right-angled bend. One of the openings may be configured as a Luer connection and may be suitable for establishing a Luer connection with a tube. The Luer connection of the opening may constitute a total volume of up to 100 cubic millimeters of the internal volume of the adapter. The internal volume of the adapter may be 570 cubic millimeters in total, and the internal volume minus the internal Luer volume may be about 467 cubic millimeters in total. These values are exemplary values, as ultimately the internal volumes may vary depending on the embodiment, as long as the goal is to achieve disconnection without drawing air into the tube section.

According to one embodiment of the invention, the disposable, in particular the tube, is a venous tube of an extracorporeal blood treatment device, in particular a dialysis device, preferably made of a polymeric material. The tube may comprise or consist of PVC as the polymeric material. The material of the tube may comprise a plasticizer.

Preferably, the volume change of the disposable, in particular of the tube, in particular of a sub-section of the tube to which negative pressure of −120 mbar, in particular −175 mbar, in particular −200 mbar, in particular −250 mbar, in particular −1000 mbar, has been applied, is smaller than a volume of the adapter when the tube is disconnected, wherein the volume of the adapter is preferably constant. In a further embodiment, the volume change of the disposable under the above conditions is greater than a volume of the adapter by 0.5 ml or by 1 ml. With this slightly larger volume change, the risk of air entry into a patient is not minimized in principle, but some standards allow entry of a small amount of air during a treatment.

Preferably, said volume change of the tube is at a temperature between 0° C. and 50° C., in particular between 30° C. and 42° C., in particular between 35° C. and 42° C., in particular at 39° C.

Furthermore, the first line section of the tube or disposable to which negative pressure is applied can have a length of 1000 mm to 2000 mm, in particular between 1500 mm and 1900 mm, in particular between 1500 mm and 1700 mm. The first line section of the tube or disposable to which negative pressure is applied may have an inner diameter of from 3 mm to 10 mm, in particular from 3 mm to 5 mm, in particular from 3.5 mm to 4.5 mm, in particular from 4.0 mm to 4.5 mm. The specified length can be a length which, in intended use, is present between one end of the tube or disposable and a machine-side controllable clamp, measured along the tube or disposable.

The compliance of the first line section or the disposable, for example, can have different values depending on the design of the overall system consisting of the volume of the adapter and the applied negative pressure. For example, the compliance of the first line section of the tube to which negative pressure is applied can be between 0.1 μl/mbar and 40 μl/mbar. Suitable tube sets used for dialysis employing the disconnection method described herein typically have a compliance of 0.4 μl/mbar to 5 μl/mbar. In particular, the first line section of the tube to which negative pressure is applied may have a compliance of 1 μl/mbar to 3.5 μl/mbar, especially 1 μl/mbar to 3 μl/mbar. Compliance may also be referred to as resilience. The compliance (C) can be measured, for example, as the volume change (ΔV) of a walled structure per change in applied filling pressure (Δp), i.e. ΔC=ΔV/Op.

The parameters of the tube and their combination are apparent to the person skilled in the art from the context of the application, as long as they take into account the teaching of the present invention that the volume change of the tube during disconnection should be less than the volume of the adapter and is achieved in that air drawn toward the tube during disconnection should not be drawn further than into the adapter. In other words, the volume change is a lower limit for the internal volume of the adapter. Of course, the internal volume of the adapter can also be larger than the volume change. In this case, the system has an additional safety margin. The person skilled in the art is also aware that compliance—as an expression of a volume change with a pressure change—can be temperature-dependent due to the material properties of polymers and knows to consider them. It is also known to the skilled person that the absolute volume change is dependent on the length and diameter of the tube section placed under pressure (positive or negative pressure).

The disposable can have a manually operated tubing clamp as a shut-off element. The manually actuated tubing clamp can be displaceable along the disposable or the tube thereof. An advantage and at the same time a disadvantage of such a manually operable, displaceable tubing clamp is that the volume change when the negative pressure is applied can be influenced by the displacement. However, such a manual interaction is error-prone in that the user may forget to close the manually operable tubing clamp or may not do so at the correct position. Therefore, the area of the disposable covered subjected to the negative pressure is preferably closed-off by a machine-side controllable tubing clamp and the parameter values given above may be related to this area of the disposable. By additionally providing the manually operable tubing clamp, the volume covered by the negative pressure can be further reduced.

The parameter values mentioned are not arbitrarily chosen parameter values, but take into account the actual conditions of, for example, a dialysis treatment. For example, the lengths mentioned are based on the distance normally required between the dialysis device as a medical device and a patient. The tube diameters also correspond to the diameters normally used. The pressure values correspond to pressure values at which, for example, no complete collapse of the tube occurs and/or at which no leaks occur along the tube lines, for example at one or more connection points of the line sections.

Furthermore, according to the invention, it can be provided that the controller is further adapted to enable a disconnection of the first and second line sections only if it is ensured that a sufficient negative pressure is present in the at least one sub-section of the line section with the displaceable member, wherein the enabling is performed either based on a detection of the negative pressure by means of a pressure sensor or based on an estimation of a time period in which a sufficient negative pressure is to be assumed after operation of the pump in the disconnection mode.

For example, the connection point of the first and second line sections may be locked if it is not enabled by the controller. If a user does not release the connection quickly enough after the negative pressure has been built up, the negative pressure can be reduced again to an insufficient level, for example due to small leaks. For example, the disconnection may be enabled when the negative pressure reaches a first threshold and the connection between the line sections may be locked again when the negative pressure falls below a second threshold. The negative pressure can be detected by means of a pressure sensor.

Alternatively or additionally, the controller can enable the disconnection after the negative pressure reaches a first threshold value for a defined time stored in the program code. This can be used to reduce the possibility of the negative pressure being reduced.

By means of the output unit of the medical device, indications can be issued to a user whether a disconnection is enabled or not.

Another aspect of the invention relates to a method for disconnecting two fluid-carrying line sections of a medical device, in particular a medical device according to the invention, configured to receive a detachable fluid-carrying first line section and having a second line section configured for connecting to the first line section, which are detachably connected to each other, wherein a displaceable member is arranged in the second line section, by means of which the line section is sub-divided a first sub-section and a second sub-section, comprising the steps of:

enclosing a fluid volume in the first line section and the second line section by means of at least a first and a second shut-off element, generating a negative pressure in a first of the two sub-sections of the second line section by means of a pump, thereby effecting an elastic deformation in and/or at the second of the two sub-sections while moving the displaceable member, and actuating the pump, wherein the controller is programmed to operate the pump in a disconnection mode to generate the negative pressure.

A method according to the invention can be understood as a method for controlling a medical device when two line sections are disconnected.

Here, the medical device may comprise at least one direct connecting line between the first sub-section and the second sub-section and a valve for opening and closing the connecting line, wherein in the context of a method according to the invention, during the release of the connection of the line sections, the at least one connecting line, preferably all existing such connecting lines of the medical device, is/are shut off.

In the context of a method according to the invention, the displaceable member is at least partially formed by a balancing system of the medical device and/or comprises and/or consists of preferably a membrane, preferably of the balancing system.

Alternatively or additionally, the displaceable member may comprise or consist of at least one movable ball and/or a piston.

Preferably, in a method according to the invention, the first line section is part of a disposable that is detachable from the medical device and the second line section is part of a device-side fluidic system, in particular of the medical device.

When carrying out a method according to the invention, sections to the greatest possible extent or completely, a physiological fluid and not blood is preferably present in the first and second line.

In addition, preferably during the execution of the method, no patient is connected to the medical device and/or the first line section and/or the second line section. Thus, there is no impact of the method on the human body.

Preferably, in the context of a method according to the invention, a disconnection of the first and second line sections is enabled only if it is ensured that a sufficient negative pressure is present in the at least one sub-section of the line section with the displaceable member, wherein the enabling preferably takes place on the basis of a detection of the negative pressure by means of a pressure sensor and/or on an estimation of a time period in which a sufficient negative pressure is to be assumed after the operation of the pump in the disconnection mode or a corresponding user input for selecting the disconnection mode.

Furthermore, in the context of a method according to the invention, the step of enclosing a fluid volume in the two line sections can comprise a manual closing of a shut-off element and/or an automatic closing of a shut-off element. For example, a tubing clamp can be closed manually or automatically.

Figure 2:
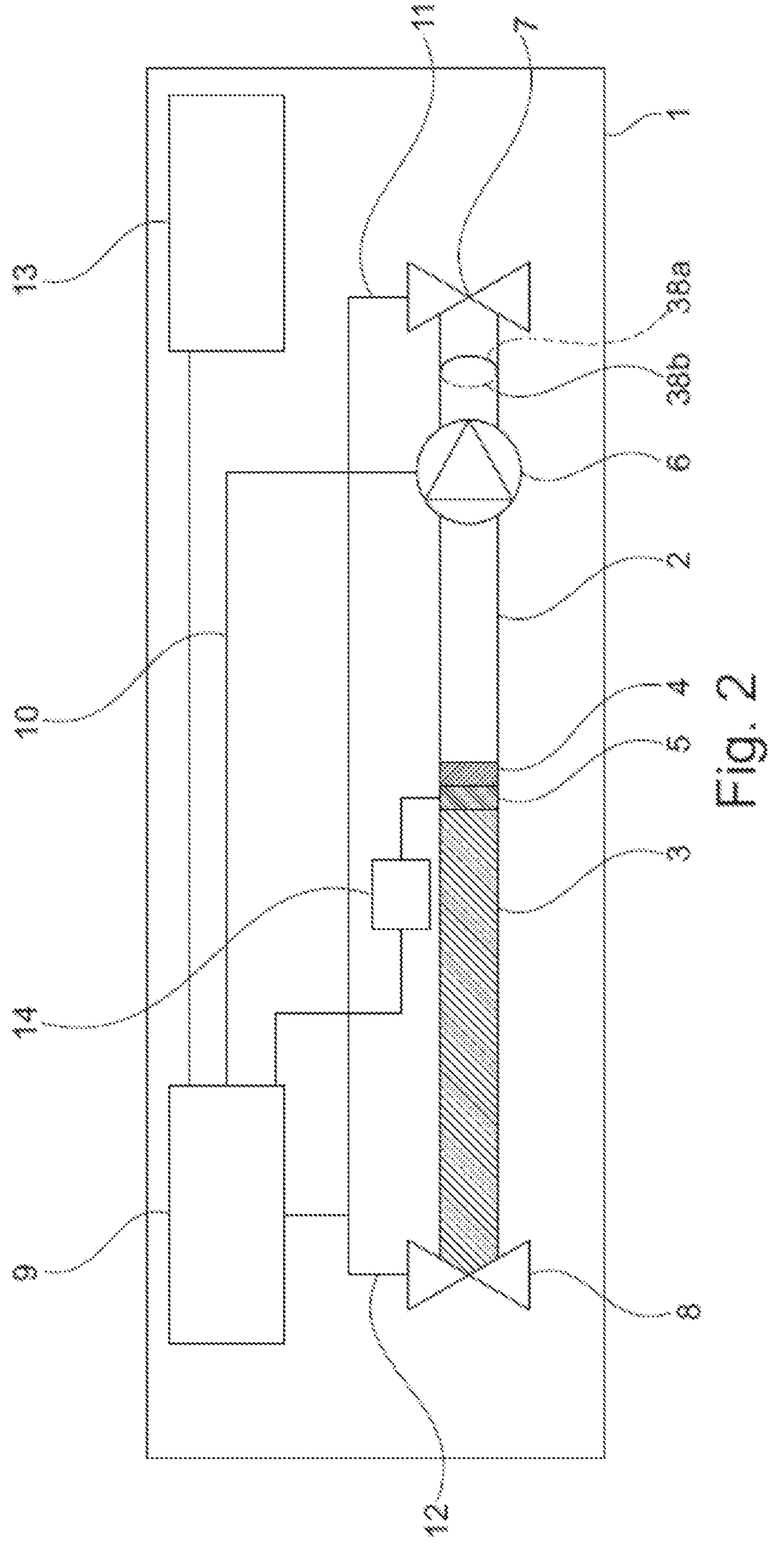
Figure 3:
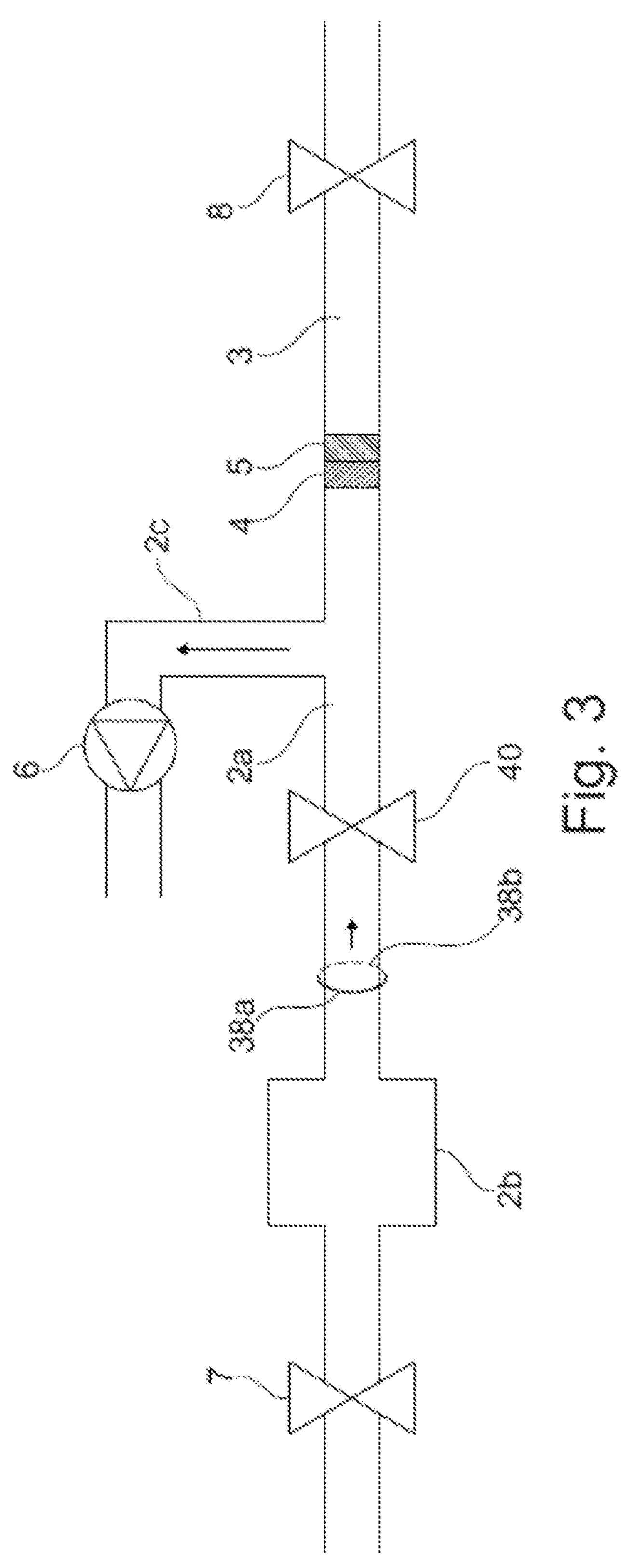
Figure 4:
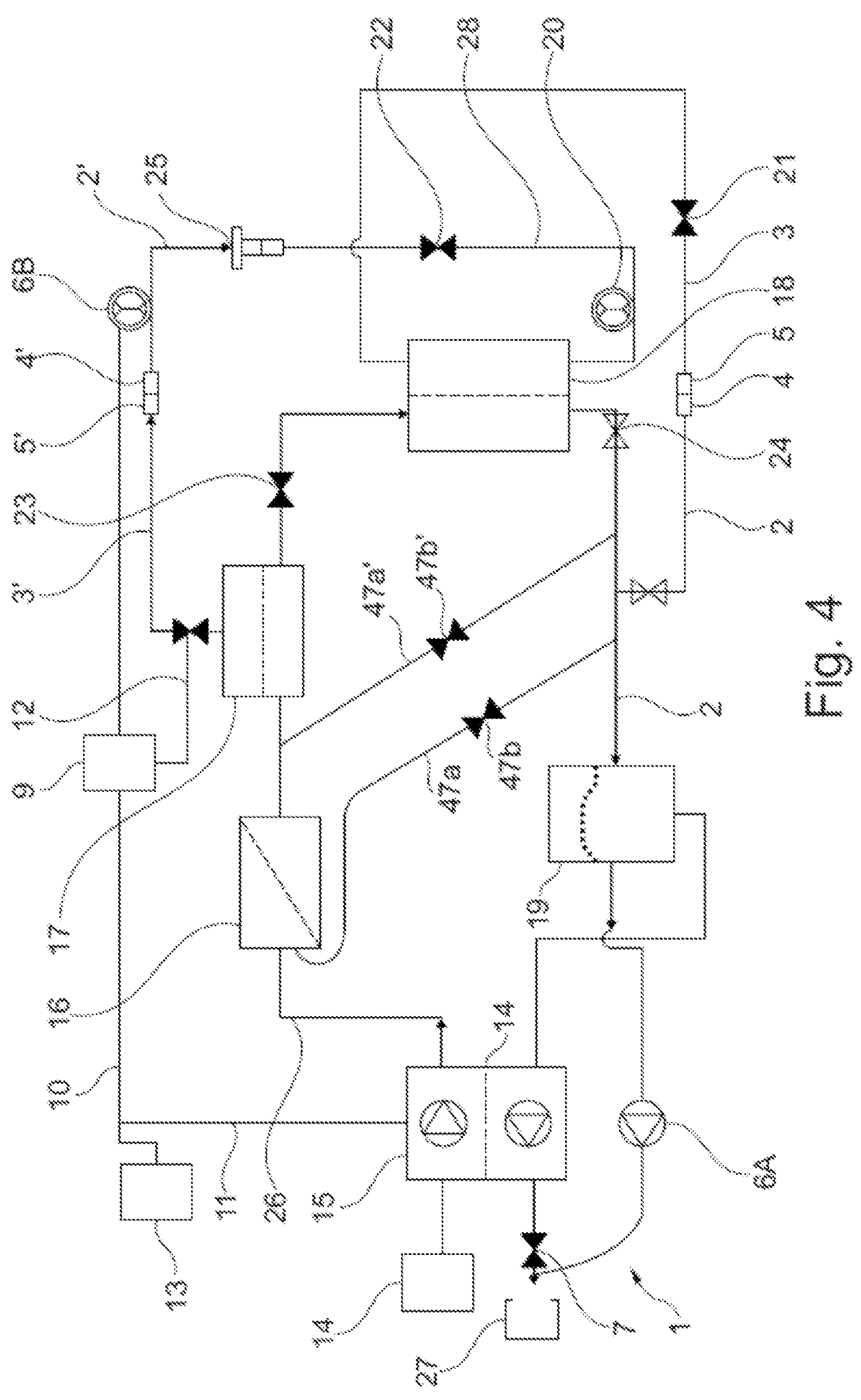
Figure 5B:
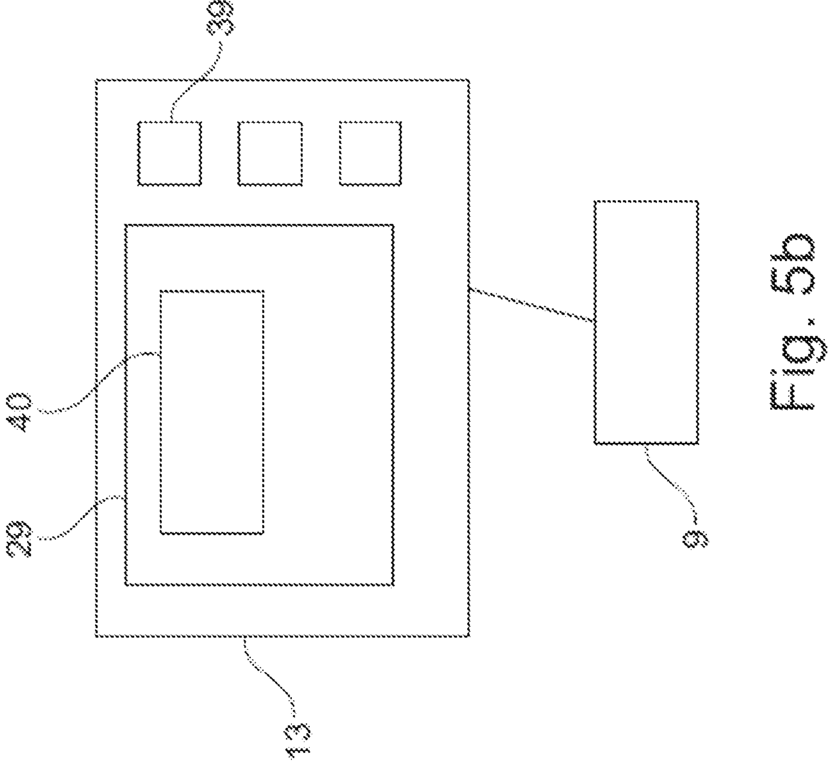
Figure 5A:
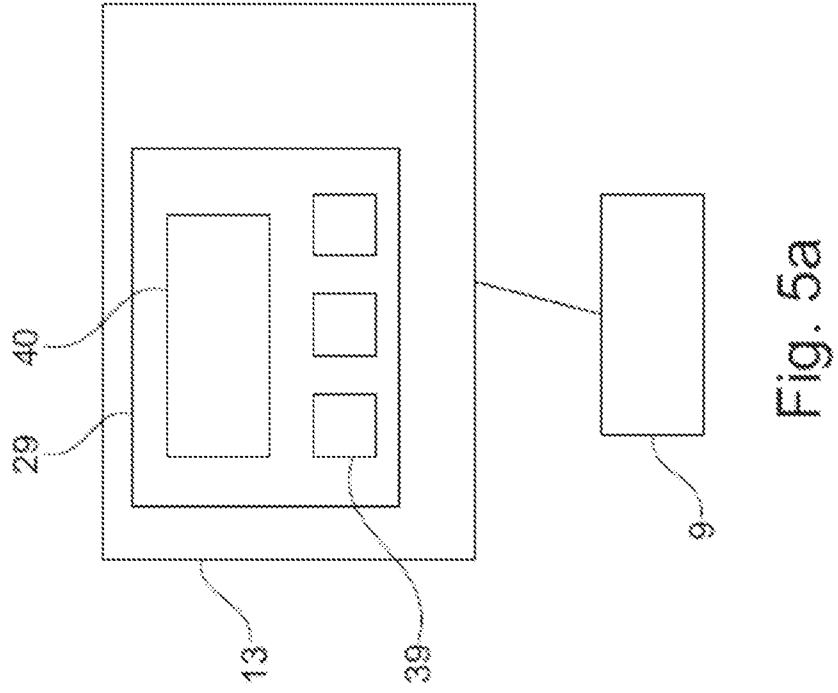
Figure 6:
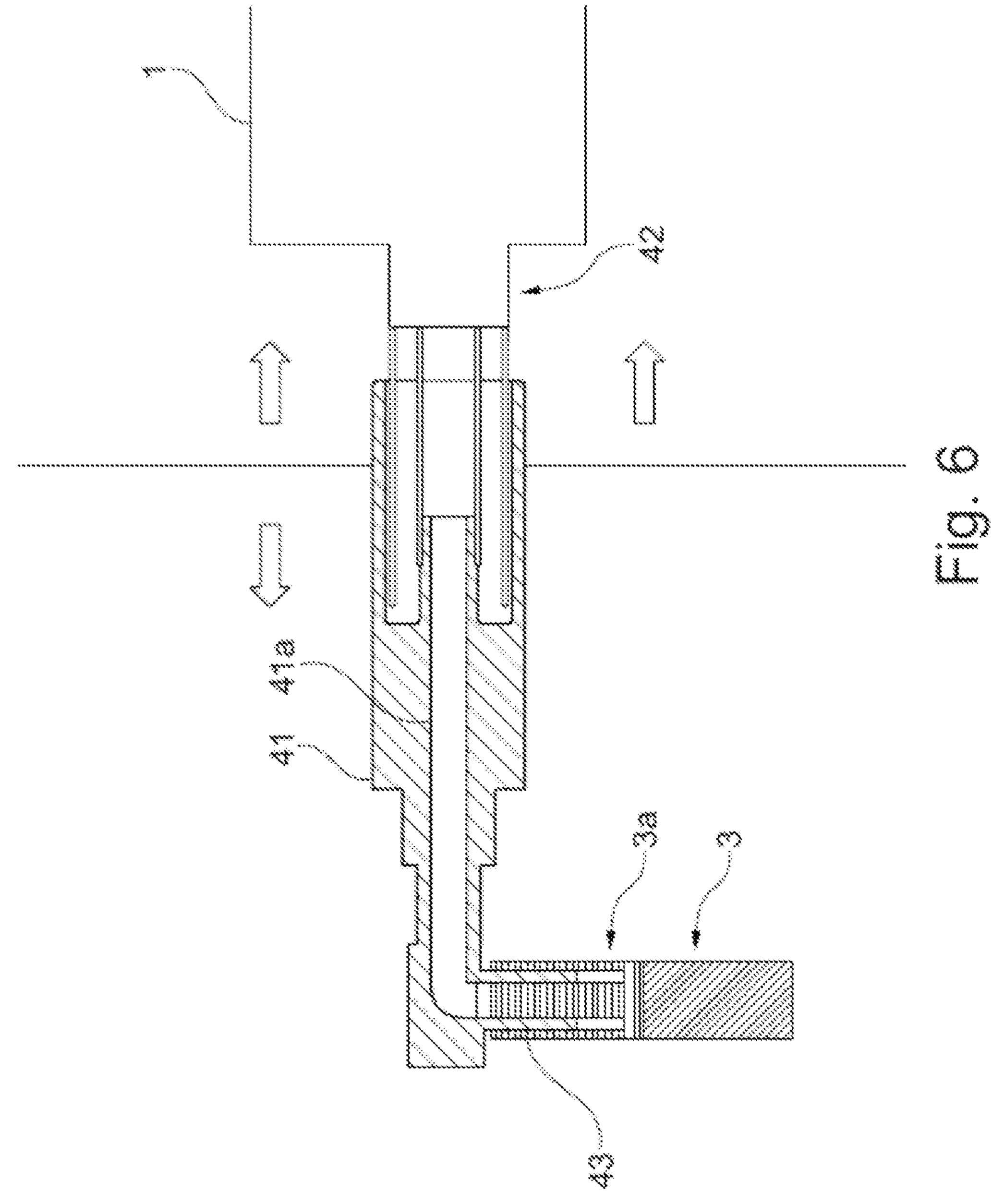
Figure 7:
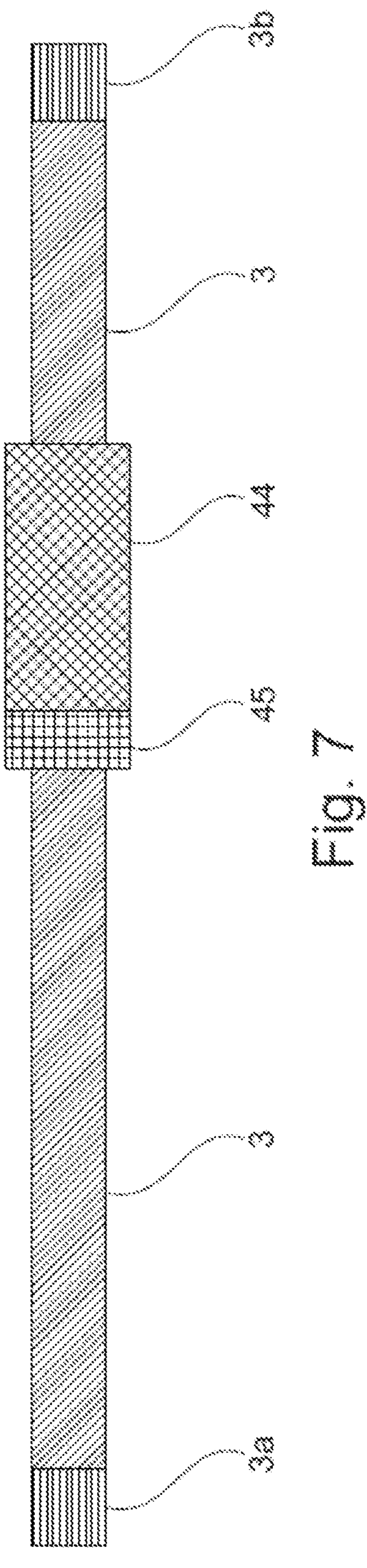
Figure 8:
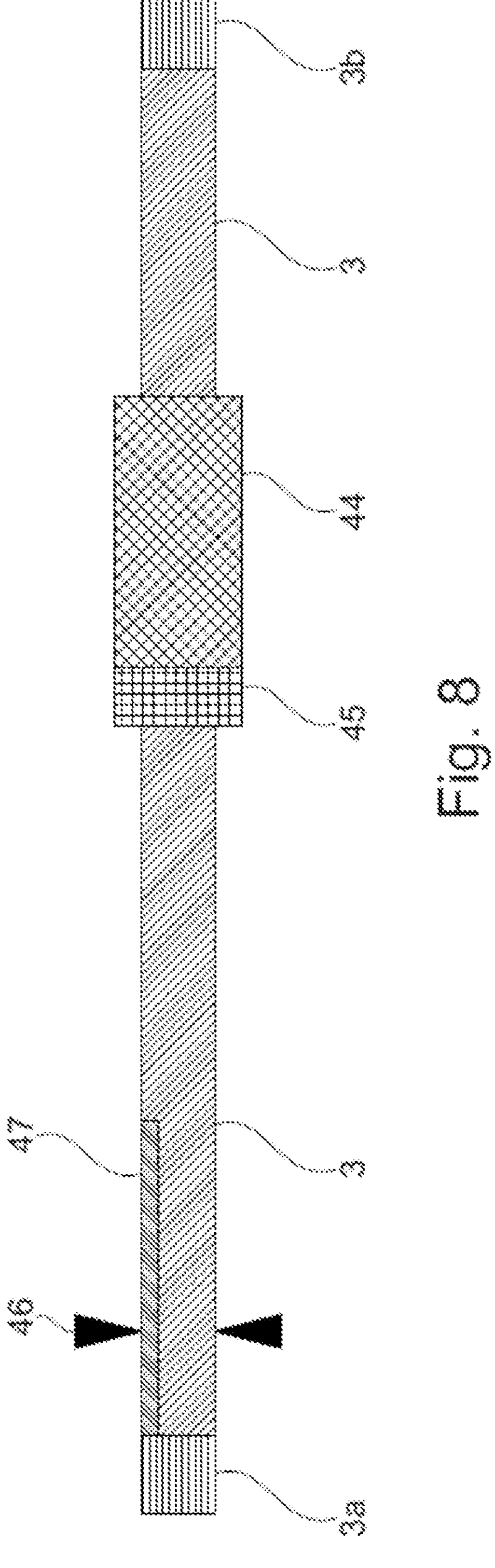
Figure 9:
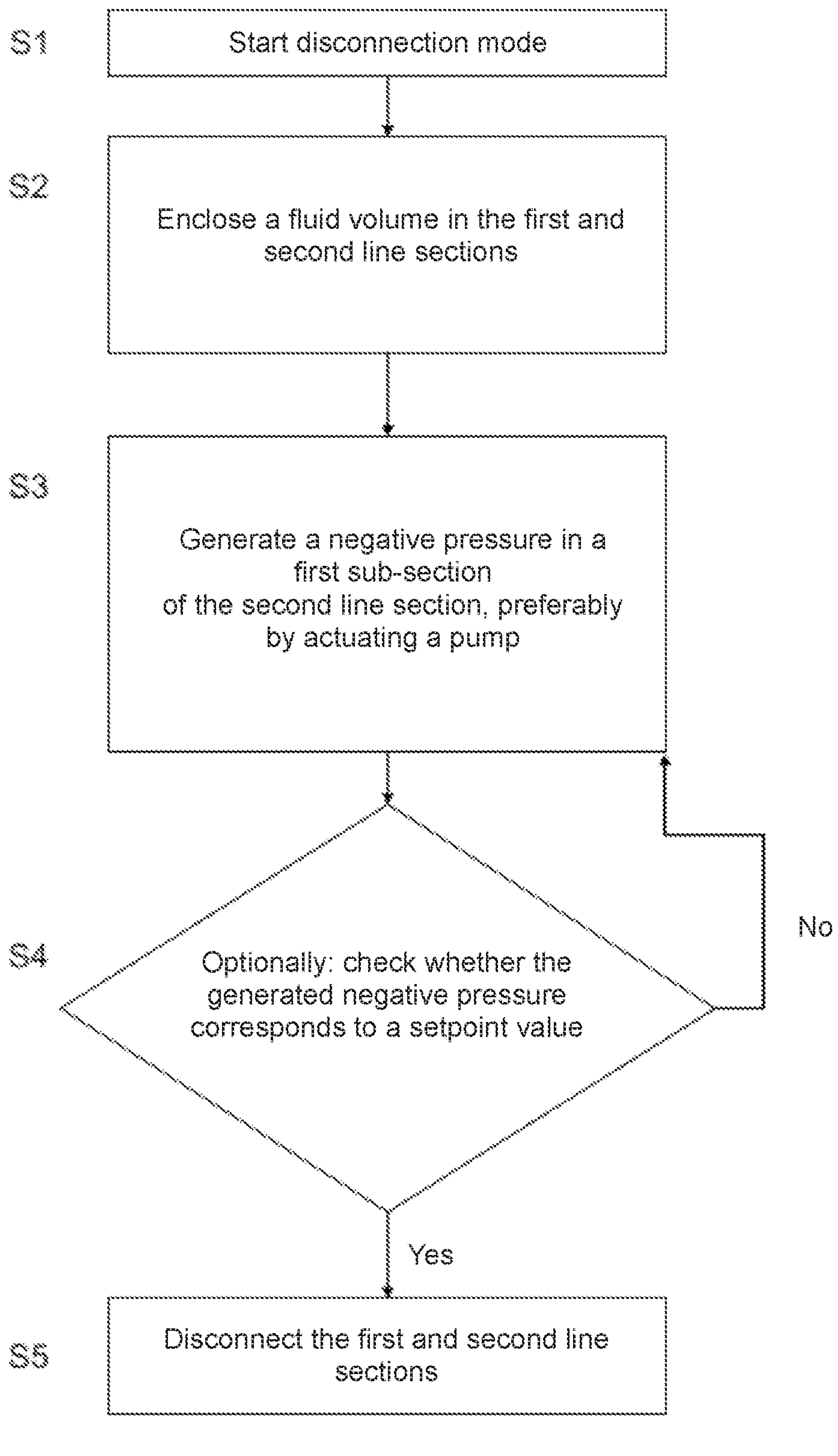

Further features and effects of the present invention will be apparent from the following description of selected embodiments of the invention with reference to the accompanying Figures, in which identical or similar components are denoted by the same reference characters. The features described below may be implemented in embodiments described further above. These embodiments described further above will not all be cited again below. Shown are in:

FIG. 1: two line sections used in the context of the method for disconnecting two fluid-carrying line sections;

FIG. 2: two line sections used in the context of the method for disconnecting two fluid-carrying line sections, and the medical device;

FIG. 3: an embodiment with a pump arranged outside the first line section;

FIG. 4: an embodiment of a medical device;

FIGS. 5*a* and 5*b*: embodiments of the user interface;

FIG. 6: a disposable according to the invention in the form of a venous tube, which is connected to a medical device by means of an adapter;

FIG. 7: a tube according to the invention according to a first embodiment;

FIG. 8: a tube according to the invention according to a second embodiment; and FIG. 9: a flow diagram of a method according to the invention.

One embodiment of the medical device 1, schematically shown in FIG. 1, has, when using the method according to the invention, two fluidically connected line sections 2, 3, which can be fluidically connected to each other, optionally via two connector elements 4, 5 of the two line sections.

Furthermore, the medical device 1 comprises a pump 6. The first and second line sections each comprise a shut-off element 7, 8 at one end. The second line section 2 comprises a displaceable member 38 which sub-divides the second line section 2 into two sub-sections 2*a* and 2*b*. The displaceable member 38 is arranged between the pump 6 and the shut-off element 7.

By means of the pump 6, a negative pressure can be generated in the first line section 2, in particular in its sub-section 2*a*. The negative pressure moves the displaceable member 38 from a first position or initial position 38*a* to a second position 38*b*, wherein a fluid volume enclosed by the first sub-section 2*a* with the displaceable member in the second position is smaller than a fluid volume enclosed by the displaceable member in the initial position.

The shut-off elements 7, 8 can be closed, thereby enclosing a fluid volume in the two line sections 2, 3. The closing of the shut-off elements 7, 8 can take place successively or simultaneously, in particular a first shut-off element can be closed first, then the negative pressure can be generated, and then the second shut-off element can be closed.

Due to the negative pressure and an elastic deformability of the second sub-section 2*b*, when the displaceable member 38 is displaced, the wall portion of the sub-section 2*b* is deformed or brought into a stressed position. Upon disconnection of the first line section 3 from the second line section 2, the wall of the second sub-section 2*b* returns to its original position and, with displacement of the displaceable member, liquid in the first sub-section 2*a* is displaced away from the point of connection toward the second sub-section 2*b*. In other words, fluid displacement can be achieved by the deformability of the second sub-section 2*b* in combination with the displaceable member.

The sub-section 2*a* may itself also have elastic deformability.

In other words, application of the negative pressure causes deformation of the second line section 2, which also includes deformation of the second sub-section 2*b*, even though the second sub-section 2*b* is not in fluidic communication with the first sub-section 2*a*.

As shown in FIG. 2, the medical device 1 may comprise a controller 9. The controller 9 may be programmed to operate the pump 6 in a disconnection mode to generate the negative pressure. Optionally, the controller 9 may also be programmed to actuate at least one or both of the shut-off elements 7, 8. For this purpose, the controller may be connected via signal lines 10, 11, 12 of the medical device 1 to the respective components to be actuated, for example pump 6, shut-off elements 7, 8. The controller 9 can, for example, be programmed to start and/or stop the pump 6.

For example, the controller may be programmed to start the pump 6 with the first valve 7 or valve 8 closed, and to close the respective other valve 7, 8, so that an enclosed volume is created in which a negative pressure is applied or in which the second sub-section 2*b* has deformed.

The medical device 1 may comprise a user interface 13. The user interface 13 may be configured for input of an instruction by a user, and the controller 9 may be programmed to activate the disconnection mode in response to an input of the instruction at the user interface 13.

The line sections 2, 3 are not both necessarily part of the medical device 1 but one or both of the line sections 2,3 may be connected to the pump 6 and the shut-off elements 7, 8 only when the medical device 1 is in use.

The medical device 1 may comprise the first line section 3 and/or the second line section 2. The first line section 3 and/or the second line section 2 may be part of a device-side fluidic system of the medical device 1.

The first line section 3 and/or the second line section 2 may be part of a disposable.

The pump 6 may be arranged along the first line section 3 and/or the second line section 2 or at a location of a fluidic system outside the two line sections 2, 3 that is in fluidic communication with the two line sections 2, 3. For example, the pump 6 may be arranged on the side of the shut-off elements 7,8 that is beyond the connectors 4,5. It need only be possible with the pump 6 to remove liquid from a sub-section of the second line section 2 with the displaceable member 38.

In the embodiment shown in FIG. 3, the pump 6 is not arranged directly in the branch of the second line section 2 that comprises the displaceable member 38 but is arranged on a branch line 2*c* that is open to the surroundings. For closing off the branch line 2*c*, a further shut-off element (not shown) can be provided or the pump 6 itself can serve as a shut-off element.

In the embodiments described in conjunction with FIGS. 1 to 3, the second sub-section 2*b* may be part of a freshwater line system, or equivalently for purposes of this invention, a dialysate inlet of the medical device 1, and the first sub-section 2*a* may be part of a wastewater line system, or equivalently for purposes of this invention, a dialysate outlet. The second sub-section 2*b* may have a larger compliance than the first sub-section 2*a* and the first line section 3 combined.

A further shut-off element 40 may be provided at the first sub-section 2*a*. Said element is open during the disconnection.

Because the displaceable member 38 fluidically separates the wastewater line system and the freshwater line system from one another, contamination of the freshwater line system by used water carried in the first and second line sections 2,3 is prevented.

FIG. 4 schematically illustrates an embodiment of the medical device 1 in the form of a dialysis device. In the Figures, some components are optional, in particular, some components may configured as disposables and do not have to be an integral part of the medical device 1.

The disconnection point may be a connection point in the outlet from the extracorporeal blood line system, for example the connection point of the first line section 3 with the second line section 2, or connector elements 4, 5 arranged at their respective ends. The embodiments or designs included in this description may also be present instead of the components and designs explicitly described herein.

The dialysis device as a medical device 1 comprises or can comprise as a medical device 1: Fluid source or liquid source 14, balancing system 15 with pump, first sterile filter (optionally) 16, second sterile filter (optionally) 17, dialyzer (optionally) 18, deaeration chamber (optionally) 19, ultrafiltration pump (optionally) 6A, priming or substituate port, e.g. in the form of the connector element 5', priming or substituate pump (optionally) 6B, outflow port e.g. in the form of the connector element 4, blood pump 20, controller 9, user interface 13, signal lines (only a selection is shown) 10, 11, 12, venous clamp 21—can be used as shut-off element 8—, arterial clamp (optionally) 22, a pre-dialyzer shut-off element 23, a post dialyzer shut-off element 24, a first discharge line shut-off element 7 (optional), a first priming line shut-off element 25.

The components may be connected to liquid-carrying lines as follows: The liquid, typically a physiological liquid or dialysate, is pumped from the liquid source 14 into a dialysate line 26 through the balancing system 15 comprising the displaceable member 38, for example in the form of a balancing chamber membrane M, and optionally through the first sterile filter 16 to the dialyzer 18 and then discarded from the dialyzer 18 into a discharge line 2, optionally through a deaeration chamber 19, back through the balancing system 15 and into a drain 27 (not part of the medical device 1).

The dialysate line 26 can have a branch line, in the form of an inlet line 3', for example optionally via a second sterile filter 17, which can lead via a priming or substituate port, i.e. the connector element 5' to a so-called priming or substituate line 2'. This priming or substituate line 2' may be connected to an arterial blood line 28. Liquid, for example blood during treatment or priming or rinsing liquid in the priming phase, in the blood line or lines 28, 2' can be pumped by means of a blood pump 20. The balancing system 15 ensures that only a predetermined amount of liquid is drawn from the patient or that no liquid is drawn.

Various balancing systems are known, for example, flow measurement can be used to determine the amount of liquid pumped to the patient and the amount pumped away from the patient, and the delta—as prescribed—can be adjusted so that a desired ultrafiltration rate, in other words net balance rate, is realized.

FIG. 4 shows another balancing system. Here, by means of a volumetric balancing system 15, for example, the same volume is pumped towards the patient as is pumped away from the patient. An ultrafiltration pump 6A, connected in parallel, additionally pumps liquid away from the patient, thus generating the net balance or ultrafiltration rate. In such a balancing system, a membrane M disposed in a volume-rigid balancing chamber may be used as a displaceable member 38. The membrane M separates a freshwater line system of the medical device from a service water line system.

As shown schematically in FIG. 4, one or more direct connecting lines 47*a*, 47*a* may be provided which connect or short-circuit a freshwater line system, i.e. a line system with fresh, uncontaminated liquid, of the medical device 1 with a service water line system, i.e. a line system with used, potentially contaminated liquid. For example, such a connecting line may extend between the first and second sterile filters 16, 17. These connecting lines 47*a*, 47*a*' are, while the medical device 1 is in the disconnection mode and/or during the disconnection process of the line sections, preferably completely shut off by means of valves 47*b*, 47*b*' arranged in the connecting lines 47*a*, 47*a*', so that contamination of the freshwater circuit is prevented.

In particular, the following components or lines may be configured as a disposable: the dialyzer 18, the arterial blood line 28, the venous line 3, the priming or substituate line 2'. These lines together may form a tube set or a cassette system. A cassette system means that at least two of these lines are non-detachably connected to each other and/or the lines are at least partially formed by dimensionally stable channels.

For example, the medical device 1 may be arranged to fill the tube set or cassette system with physiological liquid prior to treatment. For this purpose, for example, the controller 9 may be programmed, for example in a filling mode, which may also be called priming mode, to transfer liquid from the liquid source 14 via the priming or substituate port or the connector element 4' into the tube set or the cassette system by means of the pumps of the balancing system 15.

In a further method step, for example a flushing mode, after filling or also as part of filling, the tube set or the cassette system can be flushed, whereby liquid is flushed through the tube set or the cassette system and is flushed through the outflow port or the connector element 5 into the discharge line 2.

A method according to the invention can be applied, for example, to a detachment of the venous line 3 connected to each other via two connector elements 4 and 5 from the discharge line 2. As reflected by the reference characters, in this case the venous line 3 corresponds to the detachable fluid-carrying first line section 3 of FIGS. 1 to 3. The discharge line 2 corresponds to the machine-side fluid-carrying second line section 2 of FIGS. 1 to 3 in this embodiment. In this example, the pump 6 generally indicated by the reference character 6 in FIGS. 1-3 is implemented in the form of the ultrafiltration pump 6A, and the membrane M of the balancing system 15 acts as the displaceable member 38.

Alternatively or in addition, the invention can also be applied to a disconnection of the priming line 2' from the inlet line 3' which are connected to each other via two optional connector elements 4' and 5'. In this case, the substituate pump 6B is used.

The following is an exemplary description of the disconnection of the venous line 3, connected via two connector elements 4 and 5, from the discharge line 2.

For treatment, the venous line 3 is connected to the patient. For this purpose, for example in the embodiment of FIG. 4, the end of the venous line 3 that is connected with the optional connector element 5 to the connector element 4 (outflow port) of the discharge line 2 is detached from the connector element 4.

However, before this detachment takes place, which can be effected manually or automatically, the controller 9 causes a fluid volume to be enclosed in lines 2 and 3 by means of a closing of shut-off elements. The controller can, for example, actuate the ultrafiltration pump 6A and use it to pump off liquid so that a negative pressure is created. Due to the negative pressure, the displaceable member, in this case for example the membrane M of the balancing system 15 moves from the initial position to the second position. Consequently, a negative pressure is generated in the discharge line 2 by the pump 6A and, as a consequence, due to this displacement of the membrane M, a negative pressure is generated in the dialysate line 26. Thereby, an elastic deformation of the dialysate line 26 or a line element fluidically connected thereto may occur and thus the dialysate line 26 or a line element fluidically connected thereto may be transferred to a stressed position. The second line section, e.g., the discharge line 2 may also be more elastic than the first line section, e.g., the venous line 3. The line system into which the negative pressure is transmitted via the membrane may have a greater compliance than the area of the line section exposed to the negative pressure upstream of the membrane. The controller may actuate at least one, optionally multiple, shut-off elements to maintain the system in this stressed position. In case of a, optionally manual or automatic, subsequent disconnection of the venous line 3 from the connector element 4, the system can detent from the stressed position back to a relaxed position while displacing the membrane M of the balancing system 15. Fluid is thus drawn away from the connection point of the connector elements 4 and 5 into the discharge line 2.

FIGS. 5*a* and 5*b* schematically show the user interface 13. The user interface 13 may have a screen 29 and at least one button 39. The screen 29 may be a touchscreen and the button 39 may be configured as a soft key, a button to be operated on the touchscreen, as shown in FIG. 5*a*. The button 39 may also be configured as a hard key, a button provided separately from the screen, as shown in FIG. 5*b*. The controller 9 may be configured to send instructions to or receive instructions from the user interface 13 via a data line. For example, the user interface 1 may be programmed to cause the controller to switch to the disconnection mode or to start the disconnection mode after operating the button 39. The controller 9 may be programmed to perform a sequence of methods and send a message 40, for example for display, to the user interface 13 when one or more or all of the following situations occur or the controller reaches that point in the execution of a program: the program sequence permits activation of the disconnection mode, the disconnection mode may be started, disconnection may occur after the method steps to be performed on the machine side have occurred, a disinfection procedure must be performed, for example because the controller has detected that a treatment is to be prepared or performed, or a sensor, for example a pin, indicating the presence of a disposable indicates to the controller that a disposable has been removed from the machine without the method steps to be performed on the machine side having occurred.

FIG. 6 shows a disposable according to the invention in the form of a venous tube 3, which is connected to a machine-side connector 42 of the medical device 1 by means of an adapter 41. In FIG. 6, the machine-side area is indicated by the arrows to the right of the vertical line. In FIG. 6, the area outside the medical device 1 is indicated by the arrows to the left of the vertical line. The venous line 3 comprises a tube, for example made of polyvinyl chloride (PVC) or another polymer, which has at one end a connecting piece 3*a*, in this embodiment for example a Luer lock connector, by means of which the venous line can be connected to the adapter 41.

For example, the venous line 3 has a compliance of less than 500 cubic millimeters, for example 450 cubic millimeters in this embodiment. Here, a compliance of 500 cubic millimeters or 450 cubic millimeters refers to the volume by which the internal volume of the venous line 3 changes when the connection between the adapter 41 and the machine is opened. In this embodiment, the volume of the adapter 41 is, for example, more than 450 cubic millimeters, in particular 487 cubic millimeters. The volume change of the tube, in particular of its region affected by the negative pressure after the connection of the venous line 3 is opened from another line section at its end opposite to the adapter 41, is thus smaller than the volume of the adapter 41. This has the advantage that, when fluid is drawn toward the venous line 3 due to the relaxation of the tube, in particular of its region affected by the negative pressure, air is prevented from entering the venous line 3 from the machine-side connector 42. Air is allowed to enter a region 41*a* of the volume of the adapter 41. Since the volume change of the venous line 3 is smaller than the volume of the adapter 41, it is ensured that the air suctioned in the direction of the venous line 3 is not suctioned into the venous line 3 and preferably does not completely fill the volume of the adapter 41. This increases patient safety, as the risk of air bubbles in the venous line is significantly reduced.

When the venous line 3 is detached from the machine, the volume change of the venous line 3 is less than the volume of the adapter 41, in particular at an applied negative pressure of <−200 mbar, preferably <−175 mbar, particularly preferably <−120 mbar. For the purpose of this description, the indication of a negative pressure value means the pressure difference with respect to the ambient pressure. In other words, for example, the indication "negative pressure of −120 mbar" means that the pressure in the relevant line section is 120 mbar lower than the ambient pressure.

The measurement of the volume change takes place or applies in this example at a temperature of 39° C.

The region 41*a* of the volume of the adapter 41 into which air is allowed to enter may correspond to the volume from the machine-side end of the adapter to the point where the venous line or connector attached thereto terminates. With reference to FIG. 6, this can be explained in greater detail. The venous line 3 may have a connector 3*a* at one end, which is connected to the connector 43 of the adapter. The connector 43 may be or have a thread pre-stamped in the adapter, onto which the connector 3*a* can be screwed. Thereby, this connector 3*a* slides into or over the connector 43. This creates a common volume which is enclosed by both the adapter 41 or the connector 43 and the venous line 3 or the connector 3*a*. Preferably, this common volume does not belong to the region 41*a* into which air is allowed to enter. For example, the length of the adapter shown in the drawing from bottom to top, i.e., the area perpendicular to the lumen connected to the machine, may be 13 mm to 14 mm in total, but only 6 mm to 7 mm thereof may belong to the region 41*a*, since the connector 3*a* of the venous line 3 overlaps with the adapter over a length of 6 mm to 7 mm.

The adapter 41 may be configured as an integral hard plastic component with a length measured between two openings of the adapter of 4 cm to 8 cm or 5 cm to 7 cm length. The compliance of the adapter 41 may be negligibly small.

The venous line 3 may have an inner diameter of 4.3 mm and the length of the area exposed to the negative pressure may be 1900 mm starting from the Luer lock connector 3*a* to a second shut-off element (for example a tubing clamp) in this embodiment. The length of the section exposed to the negative pressure may also be 1700 mm, but at least 1000 mm, preferably at least 1500 mm. The compliance of this tube section may be less than 3.5 μl/mbar, preferably less than 3 μl/mbar and preferably more than 0.5 μl/mbar. In further embodiments, the venous line 3 may also be implemented with the parameters as mentioned in the description preceding the description of the Figures.

FIG. 7 shows a tube according to the invention, in this case the venous line 3, according to a first embodiment. At a first end, the venous line comprises the Luer lock connector 3*a*, by means of which the venous line 3 can be connected to the adapter 41. At its other end, the venous line 3 comprises a further connector 3*b*, by means of which the venous line 3 can be connected to a dialyzer, for example. The venous line 3 comprises an air separation chamber 44, for example in the form of a drip chamber, by means of which air can be removed from the venous line 3. For this purpose, the air separation chamber comprises an opening, wherein this opening may be closable, for example, by a clamp (not shown) or by a valve (not shown). Furthermore, the venous line 3 can have a clot catcher 45, for example in the form of a plastic sieve, which is preferably integrated in the air separation chamber 44 and serves to catch blood clots.

FIG. 8 shows a tube according to the invention, in this case the venous line 3, according to a second embodiment. A venous line according to this embodiment is preferably used with a manually operable tubing clamp 46 as a shut-off element. In order to assist a patient in correctly positioning the tubing clamp 46 on the venous line 3, the venous line 3 has at least one marking 47 which indicates to the patient an area in which the tubing clamp 46 is to be positioned in order to shut off the venous line 3 in a desired position and thus with a desired length. It is also conceivable to provide multiple markings to provide the patient with multiple defined positions of the tubing clamp 46. With the different position of the tubing clamp 46, for example, a different compliance of the venous line 3 can be set when a negative pressure is applied and the tubing clamp 46 closes off the venous line 3.

FIG. 9 shows a flow diagram of a method according to the invention. First, in step S1, the disconnection mode is selected, for example by a corresponding user input at the user interface shown in FIGS. 5*a* and 5*b*.

Thereupon, in step S2, the medical device is controlled, for example by controlling individual valves, in such a way that a fluid volume is enclosed in the first and second line sections which are to be detached or disconnected from each other. In this regard, the second line section may have two sub-sections separated by a movable member.

In step S3, a negative pressure is then generated in a first of the two sub-sections of the second line section, for example by actuating a pump accordingly. This negative pressure is transferred to the second of the two sub-sections by the movement of the displaceable member.

Optionally, a check can then be carried out in step S4 as to whether the negative pressure generated in step S3 corresponds to a setpoint value or falls within a tolerance range surrounding it.

If the check in step S4 yields a positive result, the first line section and the second line section are disconnected from each other in step S5.

If the check in step S4 yields a negative result, negative pressure is further generated according to step S3.

Where reference is made herein to an embodiment, this is to be understood to mean an embodiment of purely exemplary nature according to the invention.

Embodiments according to the invention can comprise one or more of the above-mentioned features in any combination, provided that the specific embodiment is not recognizable to a person skilled in the art as being technically impossible.

LIST OF REFERENCE CHARACTERS

1 medical device, for example dialysis device
2 second line section, comprising e.g. the discharge line of the dialysis device of FIG. 4
2' priming/substituate line
3 first line section comprising, for example, the venous line of the dialysis device of FIG. 4
3' inlet line
3*a* connecting piece
4 connector element connected to first line section 3
4' connector element, on the disposable side between inlet line 3' and priming/substituate line 2'
5 connector element connected to second line section 2
5' connector element, on the machine side between inlet line 3' and priming/substituate line 2'.
6 pump
6A ultrafiltration pump
6B priming/substituate pump
7 shut-off element
8 shut-off element
9 controller
10,11,12 data line
13 user interface
14 fluid source
15 balancing system
16 first sterile filter
17 second sterile filter
18 dialyzer
19 deaeration chamber
20 blood pump
21 venous clamp
22 arterial clamp
23 pre-dialyzer shut-off element
24 post dialyzer shut-off element
25 first priming line shut-off element
26 dialysate line
27 drain
28 arterial blood line
29 screen
38 displaceable member
38*a* initial position
38*b* stressed position
M membrane
39 button
40 message
41 adapter
41*a* region for air intake
42 connector
43 Luer lock connector
44 air separation chamber
45 clot catcher
46 tubing clamp
47 marking
47*a*, 47*a'* connecting line
47*b*, 47*b'* valve

The invention claimed is:

1. A medical device configured to receive a detachable fluid-carrying first line section, comprising:

a second line section configured for connecting to the first line section, wherein a displaceable member is arranged in the second line section, by means of which the second line section is sub-divided into a first sub-section and a second sub-section;

at least a first and a second shut-off element for enclosing a fluid volume in the first line section and the second line section;

a pump for generating a negative pressure in the first sub-section of the second line section, thereby effecting an elastic deformation in and/or at the second sub-section while moving the displaceable member; and a controller for actuating the pump, wherein the controller is programmed to operate the pump in a disconnection mode to generate the negative pressure.

2. The medical device according to claim 1, wherein the displaceable member is hydraulically permeable and fluidically non-permeable.

3. The medical device according to claim 2, wherein the displaceable member transfers the negative pressure generated by means of the pump from one of the first and second sub-sections to the other one of the first and second sub-sections.

4. The medical device according to claim 1, wherein the displaceable member is at least partially formed by a balancing system of the medical device and/or comprises or consists of a membrane.

5. The medical device according to claim 1, wherein the displaceable member comprises or consists of a movable ball and/or a piston.

6. The medical device according to claim 1, wherein the controller is programmed to close one of the shut-off elements to shut off the fluid volume on one side before generating the negative pressure and/or to close one of the shut-off elements to enclose the fluid volume after generating the negative pressure.

7. The medical device according to claim 1, wherein the second line section is part of a fixedly-installed device-side fluidic system of the medical device.

8. The medical device according to claim 7, comprising a fluid source fluidically connected to the second sub-section, optionally, a sterile filter fluidically disposed between and connected to the fluid source and the second sub-section, and a medical device-side connector at one end of the first sub-section for connecting to one end of the first line section.

9. The medical device according to claim 7, comprising a discharge line, wherein the first sub-section is fluidically connected to or is a part of the discharge line.

10. The medical device according to claim 9, wherein at least one direct connecting line is provided between the first sub-section and the second sub-section, and a valve is provided for opening and closing the at least one direct connecting line, and the controller is programmed to shut off the at least one direct connecting line in the disconnection mode.

11. The medical device according to claim 1, wherein the pump is a diaphragm pump.

12. The medical device according to claim 11, wherein the pump is arranged at the first sub-section.

13. The medical device according to claim 11, wherein the pump is arranged at a branch line of the first sub-section.

14. The medical device according claim 1, wherein the pump is an ultrafiltration pump and/or a blood pump and/or a substituate pump of an extracorporeal blood treatment device.

15. The medical device according to claim 14, wherein the extracorporeal blood treatment device is a dialysis device.

16. The medical device according to claim 1, comprising a user interface for input of an instruction by a user, wherein the controller is programmed to activate the disconnection mode or to start the pump in response to an input of the instruction at the user interface, and/or wherein the controller is programmed to activate a plurality of modes and to automatically perform a switchover from one of the modes to the disconnection mode.

17. The medical device according to claim 1, wherein an adapter is arranged between the first line section and the second line section, and in the disconnection mode, the controller is programmed to generate a predetermined negative pressure in the first line section, and wherein the volume change of the first line section upon application of the negative pressure is less than an internal volume of the adapter.

18. The medical device according to claim 17, wherein the adapter is made of a rigid material and has an internal volume of from 300 to 600 cubic millimeters, wherein the dimension of the adapter along its longitudinal axis preferably ranges between 1.5 cm and 3.5 cm.

19. The medical device according to claim 1, wherein the controller is further adapted to enable disconnection of the first and second line sections only when it is ensured that a sufficient negative pressure is applied in at least one of the first sub-section and the second sub-section of the second line section with the displaceable member, wherein the enabling is performed either based on a detection of the negative pressure by means of a pressure sensor or based on an estimation of a time period in which a sufficient negative pressure is to be assumed after operation of the pump in the disconnection mode.

20. Method A method for disconnecting two fluid-carrying line sections of a medical device according to claim 1, comprising the steps of:

enclosing the fluid volume in the first line section and the second line section by means of at least the first and the second shut-off element;

generating the negative pressure in the first sub-section of the second line section by means of the pump, thereby effecting the elastic deformation in and/or at the second sub-section while moving the displaceable member; and actuating the pump, wherein the controller is programmed to operate the pump in the disconnection mode to generate the negative pressure.

* * * * *